United States Patent [19]

Kageyama et al.

[11] Patent Number: 5,459,067
[45] Date of Patent: Oct. 17, 1995

[54] METHOD FOR PRODUCING OPTICALLY ACTIVE NORBORNEOL BY ESTER HYDROLYSIS

[75] Inventors: Bunji Kageyama, Ibaraki; Masanori Nakae, Toyonaka; Takayasu Sonoyama, Sakai; Kyozo Kawata, Hirakata, all of Japan

[73] Assignee: Shionogi Seiyaku Kabushika Kaisha, Dosho, Japan

[21] Appl. No.: 98,403

[22] PCT Filed: Dec. 4, 1992

[86] PCT No.: PCT/JP92/01588

§ 371 Date: Aug. 5, 1993

§ 102(e) Date: Aug. 5, 1993

[87] PCT Pub. No.: WO93/11256

PCT Pub. Date: Jun. 10, 1993

[30] Foreign Application Priority Data

Dec. 6, 1991 [JP] Japan ................... 3-349705

[51] Int. Cl.$^6$ ............... C12P 41/00; C12N 1/20
[52] U.S. Cl. ............. 435/280; 435/252.1; 435/823; 435/830; 435/875; 435/940
[58] Field of Search .................. 435/280, 252.1, 435/823, 830, 875, 940

OTHER PUBLICATIONS

ATCC Catalogue of Yeasts pp. 6, 8, 14 (1990).
Irwin, A. J., et al., "Stereoselective Horse Liver Alcohol Dehydrogenase Catalyzed Oxidoreductions of Some Bicyclic [2.2.1] and [3.2.1] Ketones and Alcohols", *J. Am. Chem. Soc.*, 98, pp. 8476–8481 (1976).
Kazlauskas, R. J., et al., "A Rule to Predict Which Enantiomer of a Secondary Alcohol Reacts Faster in Reactions Catalyzed by Cholesterol Esterase, Lipase from *Pseudomonas cepacia*, and Lipase from *Candida rugosa*", *J. Org. Chem.*, 56, pp. 2656–5665 (1991).
Narisada, M., et al., "Synthesis and In Vitro Activity of Various Derivatives of a Novel Thromboxane Receptor Antagonist, (±)–(5Z)–7–[3–endo–(Phenylsulfonyl)amino]bicyclo[2.2.1]hept–2–exo–yl]heptenoic Acid", *J. Med. Chem.*, 31, pp. 1847–1854 (1988).
Oberhauser, T., et al., "Enzymatic Resolution of Norbornane–Type Esters", *Tetrahedron*, 43, pp. 3931–3944 (1987).
Oritani, T., et al., "Microbial Resolution of (±)–Borneols", *Agr. Biol. Chem.*, 38, pp. 1961–1964 (1974).
Rabiller, C. G., et al., "Enzymatic Recognition of Diastereomeric Esters", *Tetrahedron*, 46, pp. 4231–4240 (1990).

*Primary Examiner*—Marian C. Knode
*Assistant Examiner*—S. Saucier
*Attorney, Agent, or Firm*—Fish & Neave; James F. Haley, Jr.; Kevin R. Hansbro

[57] ABSTRACT

A method for producing an optically active norborneol is provided, which includes the step of bringing a microorganism or treated cells thereof into contact with (±)-exo-norbornane type ester represented by Formula (I), wherein the microorganism is selected from the group consisting of the genus Pseudomonas, the genus Acetobacter, the genus Arthrobacter, the genus Rhodotorula, and the genus Saccharomyces. According to this method, (+)– and/or (—)-exo-norbornane type alcohol can be obtained with high yield and high purity by a simple treatment.

5 Claims, No Drawings

METHOD FOR PRODUCING OPTICALLY ACTIVE NORBORNEOL BY ESTER HYDROLYSIS

TITLE OF INVENTION

A method for producing optically active norborneol this application is a 371 of PCT/JP92/01588 filed Dec. 4, 1992.

TECHNICAL FIELD

The present invention relates to a method for producing optically active norborneol by treating exonorbornane type ester with a microorganism.

BACKGROUND ART

Among methods for producing norborneol, the following chemical synthesis method is known: Norbornane as starting material is reacted with an organic acid to form an ester of norbornane; and then, this ester is chemically deacetylated to obtain norborneol. According to such a chemical synthesis method, four kinds of stereoisomers ((+, −) - (endo, exo) - norborneol) are generated, so that complicated purification steps are required for obtaining optically active norborneol by chemical synthesis.

As a method for biologically producing norborneol, the following method is known: An ester of norbornane is brought into contact with a microorganism or reacted with an enzyme and the ester is hydrolyzed. In recent years, Th. Oberhauser et. al. reported a method for producing (−)-norborneol from (+)-norbornyl acetate by using lipass derived from Candida cylindraceae (Th. Oberhauser et. al., Tetrahedron, 43, 3931–3944 1987). Moreover, Oritani et. al. reported a method for producing (−)bornsol and (−)isoborneol from (±)bornyl acetate and (±)isobornyl acetate by using a culture of *Trichoderma sp, Trichoderma koningi, Bacillus subtilis* var. *Niger*, and *Absidia hyalospora* (T. Oritani et. al., Agr. Biol. Chemo, 38(10), 1961–1964, 1974). However, the reactions have low selectivity and thus obtained products have low optical purity. Japanese Laid-Open Patent Publication No. 2-273196 discloses an optical resolution method in which an inhibitor, for selectively inhibiting the reaction of one of the enantiomers by a biological catalyst, resolves a racemic compound. This method can be used for preparing optically active norborneol. However, this method has the following disadvantages: screening is required in order to obtain an inhibitor effective for the selection of optically active norborneol; and an inhibitor should be removed in the course of purification after the reaction, thus complicated manipulation is required. In view of these circumstances, there has been a demand for an improved biological method for obtaining optically active norborneol, in which an ester is brought into contact with a microorganism or enzyme with high stereoselectivity in the course of the hydrolysis of the ester.

DISCLOSURE OF INVENTION

According to the present invention, a method for producing optically active norborneol with high purity by treating an exo-norbornane type ester with a microorganism is provided.

A method for producing an optically active norborneol of the present invention includes the step of bringing a microorganism or treated cells thereof into contact with (±)-exo-norbornane type ester represented by Formula (I):

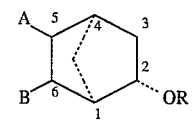

where R represents an acyl group, A and B represent independently hydrogen or A and B are taken together to form a chemical bond, wherein the microorganism is selected from the group consisting of the genus Pseudomonas, the genus Acetobacter, the genus Arthrobacter, the genus Rhodotorula, and the genus Saccharomyces.

According to the present invention, (2S)-exo-norbornane type ester is selectively hydrolyzed by bringing (±)-exo-norbornane type esters represented by the above-mentioned Formula (I) into contact with the above-mentioned microorganisms or treated cells thereof. Due to this hydrolysis, optically active alcohol and unchanged (2R)-exo-norbornane type ester are obtained.

According to the above-mentioned method, exo-norbornane type alcohol or (2R)-exo-norbornane type ester is obtained from the reaction solution.

(±)-Exo-norbornane type ester used in the present invention is represented by Formula (I):

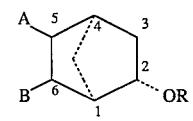

where R represents an acyl group, A and B represent independently hydrogen or A and B are taken together to form a chemical bond.

In Formula (I), the acyl group is an aliphatic acyl group with 2 to 10 carbon atoms, and preferably an aliphatic acyl group with 2 to 7 carbon atoms. Examples of the aliphatic acyl group include acetyl, propionyl, butyryl, isobutyryl, pentanoyl and hexanoyl. More preferred examples of the aliphatic acyl group include formyl, acetyl, propinonyl and isobutyryl. The acyl group may be a cycloalkyl carbonyl group with 4 to 10 carbon atoms, and more preferably a cycloalkyl carbonyl group with 4 to 7 carbon atoms. Examples of the cycloalkyl carbonyl group include cyclopropane carbonyl, cyclobutane carbonyl, cyclopentane carbonyl, and cyclohexane carbonyl. Alternatively, aryl carbonyl group, and more preferably an aryl carbonyl group with 7 to 11 carbon atoms can be used. Examples of the aryl carbonyl group include benzoyl, p-toluoyl and naphthoyl.

The above-mentioned compound is commercially available or can easily be produced by chemical synthesis. For example, norbornene is reacted with an appropriate organic acid (e.g., formic acid, acetic acid, propionic acid and butyric acid) in the presence of an acid catalyst; or a vinyl ester of an appropriate organic acid and cyclopentanediene are subjected to a Dieis-Alder reaction, whereby the desired (±)-exonorbornane type ester (I) can be obtained with high yield.

According to the present invention, a microorganism selected from the group consisting of the genus Pseudomonas, the genus Acetobacter, the genus Arthrobacter, the genus Rhodotorula and the genus Saccharomyces is used. *Pseudomonas aeruginosa, Acetobacter pasteurianus, Arthrobacter s.p, Rhodotorula pallida, Rhodotorula rubra* or *Saccharomyces sp.* are preferably used. In particular, *Acetobacter pasteurianus* and *Arthrobacter sp.* are more preferably used.

More specifically, strains such as *Pseudomonas aeruginosa* IFO 12582, *Acetobacter pasteurianus* ATCC 9432, *Acetobacter pasteurianus* ATCC 12873, *Arthrobacter sp.* SHS-0145 ( FERM BP-4060 ), *Rhodotorula pallida* IFO 0715, *Rhodotorula rubra* IFO 1101, .*Rhodotorula rubra* ATCC 2510 and *Saccharomyces sp.* SHS-20030 (FERM BP-4061) are used. The *Arthrobacter sp.* SHS-0145 and *Saccharomyces sp.* SHS-20030 were respectively deposited in the Ministry of International Trade and Industry (MITI), Agency of Industrial Science and Technology, Fermentation Research Institute, located at 1–3, Higashi/chome Tsukabashi, Ibaraki ken 305, Japan with the accession No. FERM BP-4060 and FERM BP-4061 on Nov. 2, 1992, in accordance with Budapest Treaty on the International Recognition of the Deposit of Microorganisms for the Purposes of Patent Procedure.

The above-mentioned microorganisms are grown in a medium containing nutrients generally used for growing microorganisms, such as glucose, sucrose, blackstrap molasses, polypeptone, meat extract, yeast extract, pork meat powder, soybean powder, phosphate salts, magnesium, iron and the like.

In a method of the present invention, (±)-exo-norbornane ester is brought into contact with the above-mentioned microorganism or treated cells thereof. More specifically, for example, (±)-exonorbornane type ester (I) is directly added to the culture of the above-mentioned microorganism so as to provide a concentration of 0.5 to 10% and the culture thus obtained is further cultured, whereby the ester is hydrolyzed to obtain norbornane type alcohol 2S-(II) and norbornane type ester 2R-(I). Instead of the above culture, a cell suspension or a cell extract can be used for this hydrolysis. The cell suspension is obtained by collecting cells from the culture by centrifugation, filtration, etc. and suspending the collected cells in a buffer the pH of which is to be suitable for the reaction or a buffer containing an organic solvent. The cell extract is prepared by breaking the collected cells by employing lyric enzyme or generally using ultrasonification, French press, etc. and removing cell debris by centrifugation, etc.

In the present invention, bringing (±)-exo-norbornane type ester into contact with a microorganism refers to directly adding (±)-exo-norbornane type ester to a culture; and bringing (±)-exo-norbornane type ester into contact with treated cells of a microorganism refers to adding (±)-exo-norbornane type ester to a cell suspension or a cell extract instead of the culture.

In order to allow the reaction to be efficiently conducted, (±)-ester (I) to be added can be used by being dissolved in a hydrophobic solvent such as n-hexane or a hydrophilic solvent such as dimethyl sulfoxide, methanol and ethanol so as to provide a concentration of 10 to 75%.

A reaction process of the above-mentioned hydrolysis according to the present invention is shown in the following reaction process diagram a:

(Reaction process diagram a)

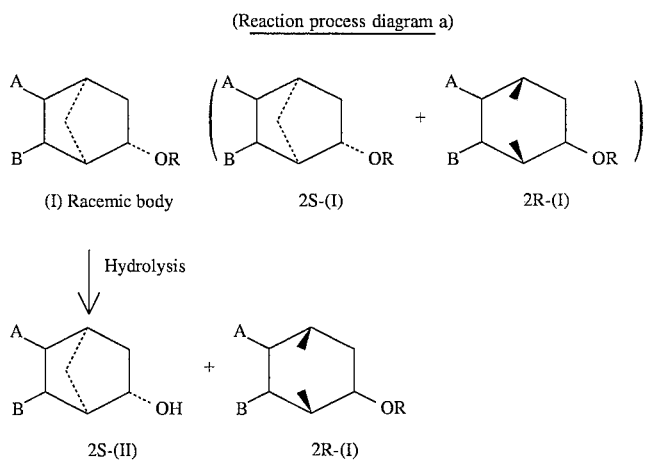

In this process diagram, R, A and B are the same as those described before.

As shown in the above-mentioned process diagram, among exo-norbornane ester, only 2S-(I) is selectively hydrolyzed and converted to exo-norbornane type alcohol 2S-(II). Most of norbornane type ester 2R-(I) remains unreacted in a reaction solution. Thus, the reaction solution containing norbornane type alcohol P2-S- (II) and norbornane type ester 2R-(I) is obtained.

Alcohol 2S-(II) thus obtained and exo-norbornane type ester 2R-(I) which remains unreacted can be separated from each other by known methods. For example, alcohol 2S-(II) and exo-norbornane type ester 2R-(I) can be separated by chromatography. In addition, it is also possible that alcohol 2S-(II) is made water-soluble by an appropriate method (e.g., alcohol 2S-(II) is reacted with an organic acid such as phthalic anhydride to form a half ester), and then alcohol 2S-(II) thus obtained can be extracted to obtain a desired optically active norbornane type compound.

Hereinafter, the case where (±) -exonorbornyl acetate is used will be described.

(Reaction process diagram b)

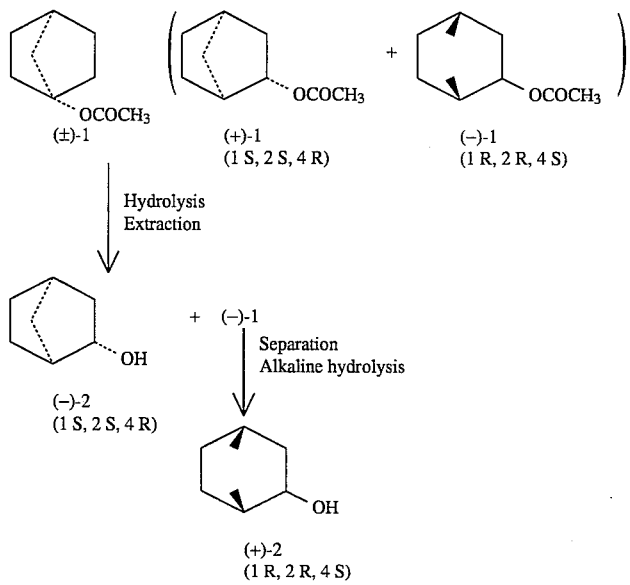

As shown in the reaction process b, 0.1 to 2 times by volume of an appropriate solvent is added to the reaction mixture obtained by the treatment of the present invention to extract norborneol(−)-2 and norbornyl acetate(−)-1. As the solvent, chloroform, dichloromethane, ethyl acetate, n-hexane, etc. can be used alone or in combination. The extracted norborneol (−)-2 and norbornyl acetate(−)-1 are appropriately concentrated. Then, 1 to 2 times by volume of an organic acid anhydride such as maleic anhydride and phthalic anhydride is added to the concentrate thus generated to form a water-soluble adduct of norborneol(−)-2 and an organic acid (maleic acid, phthalic acid, etc.). Moreover, a solution of a basic compound such as sodium bicarbonate is added to the reaction mixture to be neutralized. Then, the organic acid adduct of norborneol(−)-2 and norbornyl acetate(−)-1 shift to an aqueous layer and an organic solvent layer, respectively. The aqueous layer is separated and subjected to an alkali treatment. After this, the aqueous layer thus treated is extracted with an appropriate organic solvent such as dichloromethane and concentrated; as a result, norborneol(−)-2 with high optical purity can be obtained. Norbornyl acetate(−)-1 can be collected from the organic solvent layer, which is obtained by being separated from the aqueous layer, by concentrating the solvent layer. After the collection, norbornyl acetate(−)-1 is brought into contact with commercially available lipase, esterase, etc. or chemically deacetylated, whereby norborneol (+)-2 with high optical purity can easily be obtained.

When (−)-exo-norborneol or (+)-exo-norborneol thus obtained is purified, if desired, by known methods such as that described in Irwin A., Jones J. B.: J. Am. Chem. Soc. 98, 8476–8481 (1976), etc., an optically active substance with higher purity can easily be obtained. For example, these compounds are converted into water-soluble compounds by the above-mentioned method. Then, (−)- or (+)-phenetylamine is added to the respective compounds thus obtained to form respective phenetylamine salts, whereby an optically active substance with high purity of 98% enantiomeric excess (ee) or more can be obtained. Alternatively, these compounds can be purified by generally using column chromatography.

Hereinafter, the present invention will be described in detail by way of illustrating examples and reference examples. The present invention is not limited thereto.

EXAMPLE 1

Acetobacter pasteurjanus ATCC 9432 was inoculated into 3 L of GPBY medium (4% D-glucose, 2% polypeptone, 2% meat extract, 2% yeast extract, 0.2% potassium phosphate, 0.2% magnesium sulfate, and 0.2% calcium carbonate, pH 7.0) previously provided in a 5 L small jar fermentor and cultured at 28° C. for 24 hours. The culture was centrifuged at 1,000 G for 10 minutes to remove a solid content, and then, centrifuged at a high speed of 20,000 G for 15 minutes to collect cells. The collected cells were washed twice in a saline. As a result, 19.8 g of wet cells were obtained. The wet cells were suspended in 600 ml of phosphate buffer (0.1 M, pH 6.5). To this suspension, 12.0 g of (±)-exo-norbornyl acetate ((±)-1) was added and the mixture was allowed to react with stirring at 30° C. for one hour. In the course of the reaction, 0.1N sodium hydroxide was added in small portions to the reaction mixture and the pH of the reaction mixture was maintained at 6.5±0.2. After the completion of the reaction, 1 ml of the reaction mixture was taken. To 1 ml of the reaction mixture, 1 ml of chloroform was added to extract reaction products of norborneol(−)-2 and norbornyl acetate(−)-1. The extracts were analyzed by gas chromatography (Column for optical resolution CDX-B type (⌀0.25 mm ×30 m), column temperature of 50° C. to 210° C., manufactured by J & W Corp.), revealing that 8.5 mg/ml of exo-norbornyl acerarc, 5.2 mg/ml of (−)-(1S,2S,4R)-exo-norborneol(−)-2, and 0.3 mg/ml of (+)-(1R,2R,4S)-exo-norborneol(+)-2 were detected. The reaction mixture was extracted with toluene twice (300 ml and 100 ml). The toluene layers obtained by these extractions were attached to each other to obtain 380 ml of toluene solution. The toluene solution was concentrated to about 50 ml. Then, 4.2 g of maleic anhydride was added to the concentrated solution and allowed to react at 115° C. for 4 hours. After that, to this reaction solution, 300 ml of saturated sodium bicarbonate solution was added, stirred for 5 minutes, and allowed to stand for 10 minutes. After the reaction, an aqueous layer was separated from a toluene layer, whereby about 300 ml of an aqueous layer and about 50 ml of a toluene layer were obtained.

To 200 ml of the aqueous layer thus obtained, conc. hydrochloric acid was added, whereby the aqueous layer was made acidic. The acidic aqueous layer was extracted with 100 ml dichloromethane and concentrated to obtain 5.9 g of maleic acid compound. The maleic acid compound thus obtained was dissolved in 50 ml of methanol. Then, 4.0 g of potassium hydroxide dissolved in 50 ml of water was dropped to the solution of maleic acid compound, and allowed to react at room temperature for 30 minutes. After the completion of the reaction, the reaction product was extracted with dichloromethane and the extract was concentrated to obtain colorless crystal of (−)-(1S,2S,4R)-exo-norborneol(−)-2. Yield: 2.8 g (64%), $[\alpha]^{25}D$: −3.01° (C= 1.46, CHCl$_3$), and optical purity: 90%ee.

EXAMPLE 2

Norbornyl acetate and norborneol were extracted from 400 ml of the reaction mixture, which contains the cell suspension and (±)-exo-norbornyl acetate ((±)-1) obtained in the same way as in Example 1, with 300 ml of toluene in the same way as in Example 1. The extract was concentrated to about 50 ml. To the concentrated solution, 4.2 g of phthalic anhydride was added and allowed to react at 115° C. for 4 hours. After that, 200 ml of saturated sodium bicarbonate solution was added to the reaction solution, stirred at room temperature for about 5 minutes, and allowed to stand for 10 minutes. After the reaction, a toluene layer was separated from an aqueous layer, whereby 50 ml of a toluene layer and 200 ml of an aqueous layer were obtained. To 200 ml of the aqueous layer thus obtained rained, conc. hydrochloric acid was added, whereby the aqueous layer was made acidic. After that, the acidic aqueous layer was extracted with 100 ml of dichloromethane and the dichloromethane was distilled off to obtain 7.3 g of phthalic acid monoester. The phthalic acid monoester thus obtained was dissolved in 75 ml of ethyl acetate. After chat, 3.4 g of (−)-phenetylamine was dropped to the solution of the phthalic acid monoester to obtain 9.0 g of phenetylamine salt. The amine salt was recrystallized twice with 45 ml of ethanol. Then toluene and water were added to the crystal thus obtained, and 8.3 ml of 7.3% solution of hydrochloric acid was dropped to the crystal, and after that, the toluene layer was separated. The toluene layer was concentrated and dissolved in 20 ml of methanol. Then, 17.4% solution of sodium hydroxide was dropped to the methanol in which the toluene layer was dissolved and allowed to react at 50° C. for 2 hours. The reaction product was extracted with dichloromethane, and the extract was concentrated to obtain 1.3 g of colorless crystal of (−)-(1S,2S,4R)-exo-norborneol(−)-2. Yield: 50%, $[\alpha]^{25}D$: −3.20° (C= 1.30, CHCl$_3$), and optical purity: 98%ee.

EXAMPLE 3

First, 50 ml of the toluene layer obtained in Example 1 was concentrated under reduced pressure to obtain 4.9 g of oil-like norbornyl acetate (−)-1. This norbornyl acetate was dissolved in 50 ml of methanol. Then, 50 ml of 8% sodium hydroxide was dropped to the solution and allowed to react at 50° C. for 2 hours. After that, the reaction product was extracted with dichloromethane. The extract thus obtained was concentrated under reduced pressure to be crystallized to obtain 3.1 g of colorless crystal of (+)-(1R,2R,4S)-exo-norborneol(+)-2. Yield: 71%, and optical purity: 95%ee or more.

EXMAPLE 4

First, 1L of the GPBY medium described in Example 1 was placed in a 2 L mini-Jar fermentor, and inoculated with *Acetobacter pasteurianus* ATCC 9432, followed by being cultured at 30° C. for 24 hours. Then, 10.0 g of (±)-exo-norbornyl acetate was added to the culture and the culture was allowed to react for another 4 hours. The reaction product thus obtained was extracted with 400 ml of chloroform. The extract was subjected to gas chromatography, whereby the content of a compound contained in the extract was measured. This revealed that 10.3 mg/ml of exo-norbornyl acetate, 6.2 mg/ml of (−)-(1S,2S,4R)-exo-norborneol(−)-2, and 0.5 mg/ml of (+)-(1R,2R,4S)-exo-norborneol(+)-2 were obtained.

EXAMPLE 5

First, 20 ml of 0.1 M tris hydrochloride buffer (pH 7.2) was added to 10 g of wet cells of *Acetobacter pasteurianus* ATCC 9432 obtained in the same way as in Example 1 to prepare a cell suspension. The cells were broken by a French press. Then, 0.3 mg of deoxyribonuclease was added to about 30 ml of the lysate thus obtained. The lysate was treated on ice for 20 minutes and centrifuged at 30,000 G for 15 minutes, whereby broken cells and cell debris were removed to obtain about 22 ml of cell extract. Then, 100 mg of (±)-exo-norbornyl acetate was added to 10 ml of the cell extract and allowed to react with gentle stirring in an incubator at 30° C. for one hour. After the completion of the reaction, the reaction product was extracted with 10 ml of chloroform. The extract was subjected to gas chromatography, whereby the content of a compound contained in the extract was measured. This revealed that the concentrations of exonorbornyl acetate, (−)-(1S,2S,4R)-exo-norborneol(−)-2, and (+)-(1R,2R,4S)-exo-norborneol(+)-2 were 4.6 mg/ml, 3.0 mg/ml, and 0.3 mg/ml, respectively.

EXAMPLE 6

First, 50 ml of the GPBY medium described in Example 1 was placed in 500 ml flask and then sterilized. The medium was inoculated with a microorganism shown in Table 1 and cultured at 30° C. for 24 hours. Then, 500 mg of (±)-exo-norbornyl acetate was added to the culture and cultured for 16 hours after being sealed with a rubber stopper. The norbornyl acetate and norborneol of the culture were analyzed by gas chromatography in the same way as in Example 1. The results are shown in Table 1.

TABLE 1

| Name of microorganism | Concentrations after reaction (mg/ml) | | |
|---|---|---|---|
| | NAC* | (−)-2 | (+)-2 |
| *Pseudomonas aeruginosa* IFO 12582 | 6.80 | 1.60 | 0.28 |
| *Acetobacter pasteurianus* ATCC 9432 | 6.20 | 2.24 | 0.12 |
| *Acetobacter pasteurianus* ATCC 12873 | 5.82 | 2.52 | 0.22 |
| *Rhodotorula pallida* IFO 0715 | 6.54 | 1.47 | 0.61 |
| *Rhodotorula rubra* | 7.62 | 1.01 | 0.43 |

TABLE 1-continued

| | Concentrations after reaction (mg/ml) | | |
|---|---|---|---|
| Name of microorganism | NAC* | (−)-2 | (+)-2 |
| ATCC 2510 Saccharomyces sp. SHS-20030 (FERM BP-4061) | 7.88 | 1.04 | 0.28 |

*NAC: Exo-norbornyl acetate

TABLE 2

| | Concentrations after reaction (mg/ml) | | | (−)-2 crystal obtained by hydrolysis of NAC | |
|---|---|---|---|---|---|
| Name of microorganism | NAC | (−)-2 | (+)-2 | Optical purity | Yield* |
| P. aeruginosa IFO 12582 | 3.22 | 2.98 | 1.10 | 98.0% ee | 47% |
| Saccharomyces sp. SHS-20030(FERM BP-4061) | 3.01 | 2.88 | 1.42 | 98.2% ee | 38% |

$$\times \text{Mol yield (\%)} = \frac{\text{obtained ((−) − 2) crystal (mg)}}{\text{added ((±) − 1) (mg)} \times 1/2} \times 100?$$

EXAMPLE 7

First, 1L of the GPBY medium described in Example 1 was placed in 2 L mini-jar fermentor. Then, *Pseudomonas aeruginosa* IFO 12582 and *Saccharomyces sp.* SHS-20030 (FERM BP-4061) were respectively brought into contact with the medium and cultured at 30° C. for 24 hours. Each culture was centrifuged as described in Example 1, whereby cells in each culture were collected and washed. The cells from each culture were suspended in a 0.05 M phosphate buffer (pH 7.0) so that the optical density (660 nm) thereof be 10. (±)-exonorbornyl acetate was previously dissolved in dimethyl sulfoxide so as to give a concentration of 50 w/w%.

Next 100 ml of each cell suspension was placed in 500 ml flask, and 2.0 ml of 50% (±)-exonorbornyl acetate solution was added to each cell suspension. Each flask was sealed with a rubber stopper, and then, each cell suspension was allowed to react at 30° C. The progress of the reaction was monitored based on the added amount of 0.1N sodium hydroxide required for maintaining pH 7.0. At the end of the reaction, a small amount of the reaction mixture (0.5 ml) was taken, and a reaction product was confirmed by gas chromatography in the same way as in Example 1. At a time when about 70% of added norbornyl acetate was consumed, the reaction was terminated and 100 ml of toluene was added to the reaction mixture. Thus, norbornyl acetate and norborneol were extracted. The extract from each reaction solution was concentrated to about 25 ml. Then, 0.4 g of maleic anhydride was added to each extract and allowed to react at 115° C. for 4 hours. To each reaction solution, 25 ml of saturated sodium bicarbonate was added and stirred at room temperature for 5 minutes, followed by being allowed to stand for about 10minutes. As a result, an aqueous layer and a toluene layer were formed in each reaction solution. When the toluene layer was concentrated, oil-like (−)-exo-norbornyl acetate(−)-1 was obtained. This norbornyl acetate was dissolved in 10 ml of methanol, and 8%.sodium hydroxide was dropped to the solution thus obtained and allowed to react at 50° C. for 2 hours in alkaline condition. Then, this reaction product was extracted with 10 ml of dichloromethane. The extract was concentrated whereby (+)-(1R,2R,4S)-exo-norborneol(+)-2 was crystalized. The crystal thus obtained was analyzed by gas chromatography. The results are shown in Table 2.

EXAMPLE 8

First, 50 ml of Antibiotic medium 3 (Difco) was placed in a 500 ml flask. The medium was inoculated with *Arthrobacter sp.* SHS-0145 (FERM BP-4060) and cultured at 30° C. for 20 hours. After that, 100 mg of (±)-exo-norbornyl acetate was added to the culture, and the culture was allowed to react for another 8 hours. To this culture was added 20 ml of chloroform, whereby norbornyl acetate and norborneol were extracted. The respective contents of (−)-(1S,2S,4R)-exo-norborneol(−)-2, (+)-(1R,2R,4S)-exo-norbo in the extract were measured by gas chromatography in the same way as in Example 1. This revealed that 1.02 mg/ml of (−)-(1S,2S,4R)-exo-norborneol(−)-2 and 0.11 mg/ml of (+)-(1R,2R,4S)-exo-norborneol(+)-2 were contained in the extract.

Hereinafter, bacteriological characteristics of *Arthrobacter sp.* SHS-0145 (FERM BP-4060) will be described.

1. Morphological characteristics

Cells of this strain are Gram-positive rods and have various shapes and sizes. In an early logarithmic growth phase (bouillon agar medium, 30° C., 8–12 hours cultivation), the cells become rod-shaped with a size of 1.0–1.1×3.0–4.0 μm. In a large logarithmic growth phase, the cells become short rod (bouillon agar medium, 30° C., 24–48 hours cultivation). In a stationary phase, the cells become coccal (1.0–1.1 μm in diameter, bouillon agar medium, 30° C., 72–96 hours cultivation). Sporulation is not observed. The cells are motile.

2. Cultural properties

Growth on a bouillon agar plate (30° C., 7 days cultivation): Flat lustered circular colonies of light yellow to light yellowish white with a diameter of 1.4–1.6 mm are formed within 24 hours.

Growth on a bouillon agar slant (30° C., 7 days cultivation): The strain is moderately grown along an inoculation streak.

Growth in a bouillon soft agar (30° C., 7 days cultivation): The strain moderately grows on a surface, and the growth is observed only on the upper portion of a stab culture.

Bouillon static cultivation (30° C., 7 days cultivation): The strain mainly grows to be a thick pellicle on a surface of the culture. The broth becomes moderately turbid, and the amount of a precipitate is small. Odor is not particularly recognized.

3. Growth

Growth temperature: Possible growth temperature 10°–37° C., and optimum growth temperature 24°–32° C. (peptone water).

Heat resistance: The strain does not survive more than 30 minutes in skim milk at 63° C.

Growth pH: Possible growth pH 5.2–10, and maximum growth pH 6.0–9.[ (peptone water).

Behavior with respect to oxygen: aerobic. Growth in an anaerobic atmosphere (Gas pack®, bouillon agar plate) is not observed.

4. Composition of cell wall: meso-DAP (meso-diaminopimeric acid) is not detected.

5. G + C content of DNA: 57%

6. Main various physiological characteristics of test: Oxidative (D-glucose)

Formation of acid: Acid is produced from D-glucose, galactose, D-mannose, sucrose, trehalose, fructose ( weak ) and mannitol ( weak ) but acid is hardly produced from L-arabinose and D-xylose. Acid is not produced from lactose, ribose, sorbose, rhamnose, inositol, cellobiose, and maltose.

Litmus milk: Negative
Liquidization of gelatin: Negative
VP reaction: Negative
MR reaction: Negative
Production of hydrogen sulfide: Negative
Utilization of citric acid: Positive (Christensen medium, Simmons medium)
Utilization of inorganic N source: Ammonium salt and nitrate are utilized.
Urease: Positive
Catalase: Positive
Oxidase: Positive
DNase: Negative
Reduction of methylene blue: Positive 7. Source of Isolation: soil in Japan Hereinafter, microbiological characteristics of *Saccharomyces sp.* SHS-20030 (FERM BP-4061) used in Examples 6 and 7 will be described.

1. Morphological characteristics

Shape: This strain is a yeast in a spherical or oval shape of 3.5–4.5×5–6 μm and mainly grows by budding. Multipolar budding is observed (malt extract agar medium, 28° C., 3 days cultivation). Mycelium is not observed.

Ascospore: One to four spores in a spherical shape or nearly oval shape are formed (Gorodokawa agar medium, 28° C., 10 days cultivation).

2. Assimilation and fermentation of sugar

The assimilation and fermentation of cose, galactose, sucrose, maltose and raffinose are recognized. The assimilation and fermentation of lactose, cellobiose, and starch are not recognized.

3. Other Physiological test
Assimilation of paraffin: Negative
Assimilation of Potassium nitrate: Negative
Breakdown of arbutin: Negative
Demand for vitamin: None

INDUSTRIAL APPLICABILITY

The method for using the optically active norbornane type alcohol obtained according to the present invention will be described in the following reference examples.

Reference Example 1

First, 2.8 g ( 0. 025 moles ) of (–)- (1S, 2S, 4R )-exo-norborneol obtained in Example 1 was dissolved in 56 ml of methylene chloride. To this mixture, 8.1 g of pyridinium chlorochromate (PPC) (1.5 molar ratio) and 1 g of molecular sieve 4A® were added and allowed to react at a temperature of 25 to 30° C. for one hour. The reaction solution was diluted with 56 ml of toluene, after which the reaction solution was passed through a column of 28 g silica gel, whereby a substance which was not dissolved was removed. When the effluent solution was concentrated to be dried, crude (+)-norcamphor was obtained as white crystalline powder. The (+)-norcamphor thus obtained was dissolved in 45 ml solution of tetrahydrofuran. The solution thus obtained was dropped to 30 ml solution of tetrahydrofuran of LDA (1.1 molar ratio) at −10° to −15° C. The solution thus obtained was allowed to react for 20 minutes at −10° to −15° C. After that, 3.3 g of allyl bromide (1.1 molar ratio) was dropped to the reaction solution at 0° C. or less and allowed to react at room temperature for 3 hours. The reaction solution was flown into 70 ml of ice water and was made acidic with dilhydrochloric acid solution. After that, the reaction solution was twice extracted with 50 ml of toluene. The toluene layer was washed with water and the solvent was distilled off under reduced pressure. As a result, crude (+ ) -exo-3-(2-propenyl ) bicyclo [ 2,2,1 ] heptane-2-on was obtained as an oily residue. The (+ ) -exo-3 - ( 2-propenyl ) -bicyclo [ 2,2, 1 ] heptane-2-on was purified by collecting fractions at a boiling temperature in the range of 92° to 103° C./ to 12 mmHg under reduced pressure. Yield: 3.07 g (82%), chemical purity (GC): 98.6%, Endo isomer: 0.4%, optical purity (HPLC): 90%ee, and specific rotation: $[\alpha]^{25}D+84.6°$ (C= 1.0, $CHCl_3$).

Reference Example 2 .

The reaction and treatment were conducted by using (–)-(1S,2S,4R)-exo-norborneol obtained in Example 2 in the same way as in Reference Example 1. The crude product was purified by distillation under reduced pressure, and fractions were collected at a boiling point in the range of 74° to 86° C. /3 to 4 mmHg to obtain desired (±)-exo-3-(2-propenyl)-bicyclo[2,2,1]heptane-2-on. Yield: 1.38 g (78%), chemical purity (GC): 98.8%, Endo isomer: 0.9%, optical purity (HPLC): 98%ee, specific rotation: $[a]^{25}D + 89°$ (C = 1.286, CHCl3), IR(Film) 3060, 1740, 1640, 1460, 1440, 1310, 1090 $cm^{-1}$. $^1H$ NMR($CDCl_3$) δ1.30–2.00(m, 8H), 2.5–2.6(m, 3H) δ4.90–5.20(m, 2H), 5.7–5.9(m, 1H).

The compounds obtained in the above-mentioned reference examples can be used by the method (J. Med. Chem. 31(9), 1847–1854(1988) ) as $TXA_2$ receptorantagonist which is pharmaceutically useful.

We claim:
1. A method for producing a (2S)-exo-norborneol or

(2R)-exo-norbornane type ester comprising the steps of bringing a microorganism or cell extract or cell suspension thereof into contact with a (±)-exo-norbornane type ester of the Formula (I):

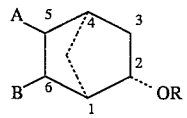

where R is an acyl group, A and B are independently hydrogen or A and B form a chemical bond,
  wherein the microorganism is selected from the group: consisting of *Pseudomonas aeruginosa, Acetobacter pasteurianus, Arthrobacter sp.* SHS-0145, *Rhodotorula pallida, Rhodotorura rubra,* and *Saccharomyce sp.* SHS-20030, and recovering the (2S)-exo-norborneol or (2R)-exonorbornane type ester.

2. The method according to claim 1, wherein R is an acetyl group.

3. The method according to claim 1 or 2 wherein the microorganism is *Acetobacter pasteurianus*.

4. The method according to claims 1 or 2, wherein the microorganism is *Arthrobacter sp.* SHS-0145 (FERM No. BP4060).

5. A biologically pure culture of *Arthrobacter sp.* SHS-0145 (FERM No. BP4060).

* * * * *

UNITED STATES PATENT AND TRADEMARK OFFICE
CERTIFICATE OF CORRECTION

PATENT NO. : 5,459,067
DATED : October 17, 1995
INVENTOR(S) : Kageyama, Nakae, Sonoyama, and Kawata It is certified that error appears in the above-indentified patent and that said Letters Patent is hereby corrected as shown below:

On the title page, Assignee section, please change: "Shionogi Seiyaku Kabushika Kaisha" to --Shionogi Seiyaku Kabushiki Kaisha--.

At column 3, in Reaction process diagram a, please change both structures labeled 2R-(I) (in the top and bottom row) as follows:

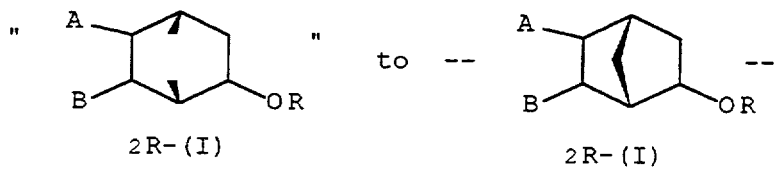

UNITED STATES PATENT AND TRADEMARK OFFICE
CERTIFICATE OF CORRECTION

PATENT NO. : 5,459,067
DATED : October 17, 1995
INVENTOR(S) : Kageyama, Nakae, Sonoyama, and Kawata It is certified that error appears in the above-indentified patent and that said Letters Patent is hereby corrected as shown below:

At column 5, in Reaction process diagram b, please change the structures for the compounds labeled (-)-1 (1R, 2R, 4S) and (+)-2 (1R, 2R, 4S) as follows:

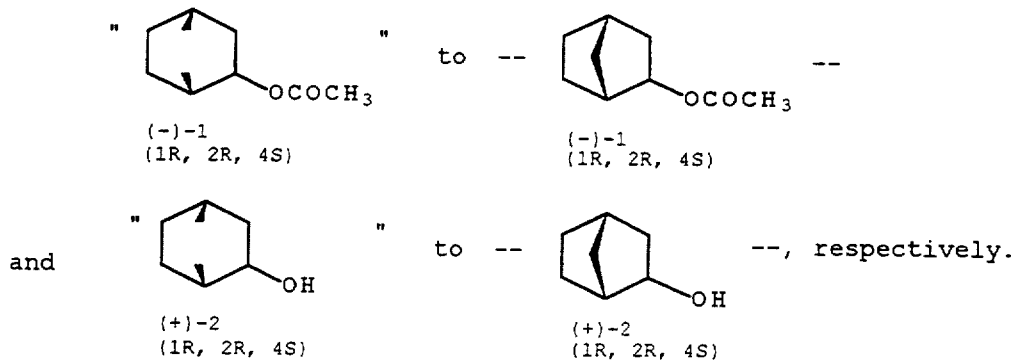

At column 10, in the footnote directly beneath Table 2, please change "X" to --*--; and please delete "?".

Signed and Sealed this

Twenty-fourth Day of September, 1996

Attest:

BRUCE LEHMAN

Attesting Officer     Commissioner of Patents and Trademarks